United States Patent [19]

Seidel et al.

[11] Patent Number: 4,575,378
[45] Date of Patent: Mar. 11, 1986

[54] SUBSTITUTED 4-AMINO-3-NITROPHENOLS, PROCESSES FOR THEIR PREPARATION AND HAIR-COLORING AGENTS CONTAINING THESE COMPOUNDS

[75] Inventors: Winfried Seidel, Obertshausen; Thomas Oelschläger, Norderstedt; Wolfgang Schlenther, Hamburg, all of Fed. Rep. of Germany

[73] Assignee: Hans Schwarzkopf GmbH, Hamburg, Fed. Rep. of Germany

[21] Appl. No.: 572,028

[22] Filed: Jan. 19, 1984

[30] Foreign Application Priority Data

Jan. 28, 1983 [DE] Fed. Rep. of Germany ....... 3302817

[51] Int. Cl.$^4$ .......................... A61K 7/13; C07C 87/60
[52] U.S. Cl. ............................................ 8/414; 8/421; 564/441
[58] Field of Search ...................... 564/441; 8/421, 414

[56] References Cited

U.S. PATENT DOCUMENTS 2,750,326  6/1956  Eckardt .............................. 564/441
4,125,601  11/1978  Bugant et al. ...................... 564/441

FOREIGN PATENT DOCUMENTS 1210810  11/1970  United Kingdom ................ 564/441
2104895  3/1983  United Kingdom ................ 564/441

OTHER PUBLICATIONS

Van Erp, Chem. Abstracts, vol. 24, p. 4282, *Halogenated Nitrophenols.*

Primary Examiner—Charles F. Warren
Assistant Examiner—John A. Sopp
Attorney, Agent, or Firm—Beveridge, DeGrandi & Weilacher

[57] ABSTRACT

The invention relates to new 3-nitro-4-aminophenols of the formula (I)

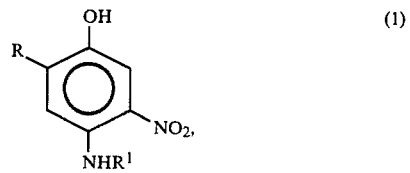

in which R denotes hydrogen or halogen, preferably chlorine or bromine, and R' denotes hydrogen or alkyl, hydroxyalkyl, dihydroxyalkyl or halogenohydroxyalkyl which has 1 to 6 carbon atoms and is straight-chain or branched, with the proviso that, if R is hydrogen, R' does not denote hydrogen, methyl or β-hydroxyethyl.

Processes for their preparation: (a) by reacting corresponding 3-nitro-4-aminophenols with certain halogenoalkyl chloroformates and subsequent basic treatment of the process products, or (b) by reacting corresponding 4-halogeno-3-nitrophenols with certain amines, and the intermediate products obtained and coloring agents for keratinic fibres, preferably for human hair, which contain at least one compound of the formula (I).

9 Claims, No Drawings

SUBSTITUTED 4-AMINO-3-NITROPHENOLS, PROCESSES FOR THEIR PREPARATION AND HAIR-COLORING AGENTS CONTAINING THESE COMPOUNDS

The invention relates to new substituted 4-amino-3-nitrophenols, processes for their preparation, hair-colouring agents containing these compounds and new intermediate products for these compounds.

The invention is based on the object of providing new dyestuffs, processes for their preparation, hair-colouring agents containing these compounds and new intermediate products for these compounds, the dyestuffs and the hair-colouring agents being distinguished from the dyestuffs and hair-colouring agents known hitherto in that they avoid the disadvantages known from the prior art and can be used to produce dyeings of high fastness to light, high resistance to rubbing and exceptionally good fastness to washing, and also have a very good storage stability.

The invention relates to substituted 4-amino-3-nitrophenols according to claim 1, processes for their preparation according to claim 2, hair-colouring agents containing these compounds, according to claims 4 to 8, and intermediate products according to claim 3.

Examples which may be mentioned of 4-amino-3-nitrophenols which fall under the general formula (I)

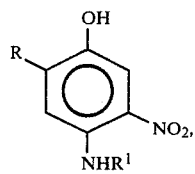
(I)

in which R denotes a hydrogen atom or a halogen atom, preferably chlorine or bromine, and R' denotes a hydrogen atom, alkyl, hydroxyalkyl, dihydroxyalkyl or halogenohydroxyalkyl, with the proviso that, if R denotes a hydrogen atom, R' may not be a hydrogen atom, methyl or betahydroxyethyl, and the alkyl radicals mentioned contain 1 to 6 carbon atoms and are straight-chain or branched, are: 3-nitro-4-ethylaminophenol, 3-nitro-4-(n-propyl)-aminophenol, 3-nitro-4-(n-pentyl)aminophenol, 3-nitro-4-(α-methyl-β-hydroxyethyl)aminophenol, 3-nitro-4-(α-chloromethyl-β-hydroxyethyl)aminophenol, 3-nitro-4-(α-ethyl-β-hydroxyethyl)aminophenol, 3-nitro-4-(β-hydroxypropyl)aminophenol, 3-nitro-4-(γ-hydroxypropyl)aminophenol, 3-nitro-4-(β,γ-dihydroxypropyl)aminophenol, 3-nitro-4-(β-hydroxy-n-butyl)aminophenol, 3-nitro-4(β-hydroxy-n-hexyl)aminophenol, 6-bromo-3-nitro-4-aminophenol, 6-bromo-3-nitro-4-methylaminophenol, 6-bromo-3-nitro-4-ethylaminophenol, 6-bromo-3-nitro-4-(n-propyl)aminophenol, 6-bromo-3-nitro-4-(n-pentyl)aminophenol, 6-bromo-3-nitro-4-(β-hydroxyethyl)aminophenol, 6-bromo-3-nitro-4-(α-methyl-β-hydroxyethyl)aminophenol, 6-bromo-3-nitro-4-(α-chloromethyl-β-hydroxyethyl)aminophenol, 6-bromo-3-nitro-4-(α-ethyl-β-hydroxyethyl)aminophenol, 6-bromo-3-nitro-4-(α-hydroxypropyl)aminophenol, 6-bromo-3-nitro-4-(γ-hyroxypropyl)aminophenol, 6-bromo-3-nitro-4-(β,γ-dihydroxypropyl)aminophenol, 6-bromo-3-nitro-4-(β-hydroxy-n-butyl)aminophenol, 6-bromo-3-nitro-4-(β-hydroxy-n-hexyl)aminophenol, 6-chloro-3-nitro-4-aminophenol, 6-chloro-3-nitro-4-methylaminophenol, 6-chloro-3-nitro-4-ethylaminophenol, 6-chloro-3-nitro-4-(n-propyl)aminophenol, 6-chloro-3-nitro-4-(n-pentyl)aminophenol, 6-chloro-3-nitro-4-(β-hydroxyethyl)aminophenol, 6-chloro-3-nitro-4-(α-methyl-β-hydroxyethyl)aminophenol, 6-chloro-3-nitro-4-(α-chloromethyl-β-hydroxyethyl)aminophenol, 6-chloro-3-nitro-4-(α-ethyl-β-hyroxyethyl)aminophenol, 6-chloro-3-nitro-4-(β-hydroxypropyl)aminophenol, 6-chloro-3-nitro-4-(γ-hydroxypropyl)aminophenol, 6-chloro-3-nitro-4-(β,γ-dihydroxypropyl)aminophenol, 6-chloro-3-nitro-4-(β-hydroxy-n-butyl)aminophenol and 6-chloro-3-nitro-4-(β-hydroxy-n-hexyl)aminophenol.

The compounds of the general formula (I) can be prepared by processes analogous to processes which are known per se. General preparation processes are given below, by way of example, for compounds of the formula (I).

GENERAL PREPARATION PROCESS A

The compounds of the formula (I) are obtained by reacting compounds of the formula (II)

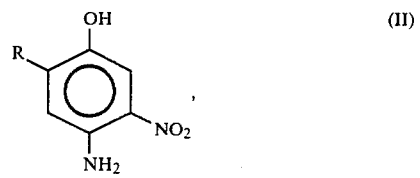
(II)

wherein R has the meaning given, with halogenoalkyl chloroformates of the formula (III)

(III)

wherein R" is a straight-chain or branched alkyl radical which has 2 to 6 carbon atoms and contains at least one halogen atom, preferably chlorine or bromine, in the beta- or gamma-position, in the presence of bases to give compounds of the formula (IV)

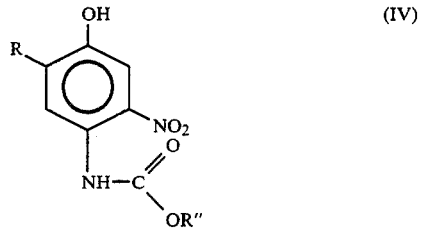
(IV)

and by subsequent intramolecular alkylation (to cyclic carbamates, which are generally not isolated) and decarboxylation of these intermediate products by means of a base. (The halogenoalkyl chloroformates of the formula (III), some of which are not yet described in the literature, are prepared by reacting correspondingly halogenated hydroxyalkanes with phosgene at temperatures of about 0° C., if appropriate in the presence of catalysts). The process is usually carried out in two stages, but can also be carried out as a one-pot process.

Stage 1:

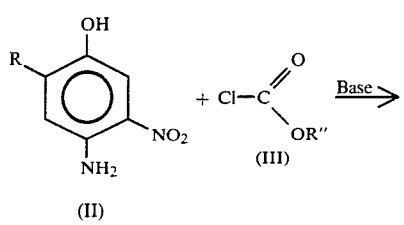

(II)   (III)

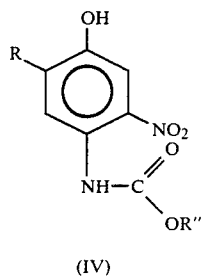

(IV)

Examples of bases which can be used here are: alkali metal carbonates and bicarbonates and alkaline earth metal carbonates and bicarbonates, alkaline earth metal oxides, triethylamine and similar organic bases. The reaction is carried out in the presence of organic solvents, such as, for example, toluene, chlorobenzene, dioxane, dimethoxyethane and the like, which are inert in the reaction. If appropriate, these solvents may also be combined with water. The temperature is about 70° C. or more, up to the reflux temperature of the solvent used. In this process, the starting compound is taken with the base (in a slight excess) in the solvent and the halogenoalkyl chloroformate is then added dropwise at 70° C. For working up, the mixture is filtered hot, if appropriate, and the filtrate is either concentrated or poured onto water, after which the intermediate products of the formula (IV) in each case precipitate.

Stage 2:

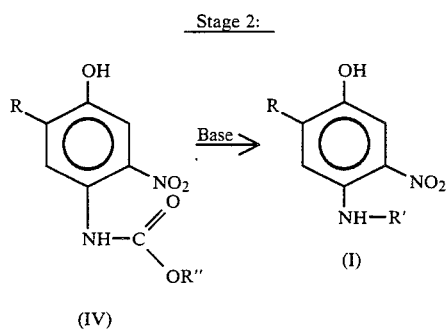

(IV)   (I)

Bases which can be used are alkali metal hydroxides or alkaline earth metal hydroxides. Water or ethanol or mixtures thereof are used as solvents. The intermediate product of the 1st stage is brought together with 4 to 4.5 moles of base at room temperature and the mixture is then heated at about 60°–80° C. After neutralisation, the product precipitates directly or is obtained by concentration (salts being removed).

GENERAL PREPARATION PROCESS B

The compounds of the formula (I) can be prepared by reacting halogenated nitrophenols of the formula (V)

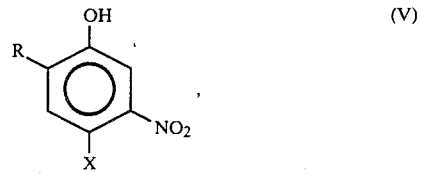

(V)

wherein R has the meaning given and X is halogen, preferably fluorine or chlorine, with alkyl-, hydroxyalkyl- or dihydroxyalkyl-amines which contain 1 to 6 carbon atoms in the alkyl, hydroxyalkyl or dihydroxyalkyl radical and are straight-chain or branched. The starting compound is taken with an excess of one of the amines mentioned and with a base (suitable bases are alkali metal hydroxides, carbonates and bicarbonates and alkaline earth metal hydroxides, carbonates and bicarbonates, triethylamine and similar organic amines) at room temperature and the mixture is then heated in a bath up to a bath temperature of 100°–140° C., if appropriate in the presence of a catalyst, such as, for example, copper-I chloride. After a few hours, the mixture is cooled, acidified with, for example, hydrochloric acid and extracted with an organic solvent (for example methylene chloride, ethyl acetate, benzene or the like). The organic phase then contains unreacted starting material. The aqueous phase is now neutralised, and extracted again. The desired product is contained in these organic extracts and is obtained by concentration and, if appropriate, purified by recrystallisation.

New compounds of the formula (I) and their preparation are described in examples below, without the selection of the examples denoting a restriction.

EXAMPLE 1

Preparation of 4-(γ-hydroxypropyl)-amino-3-nitrophenol

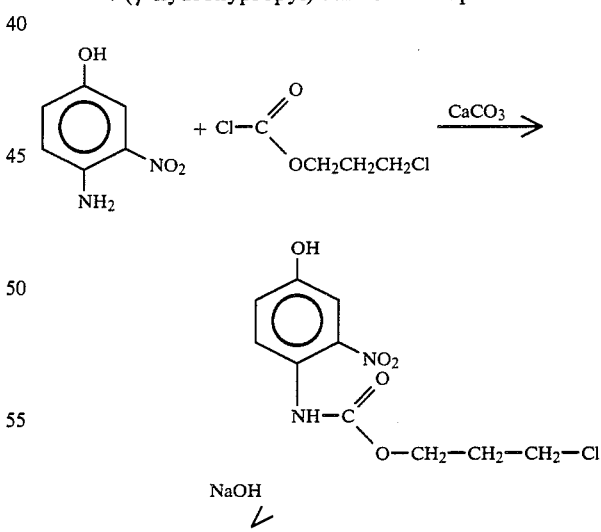

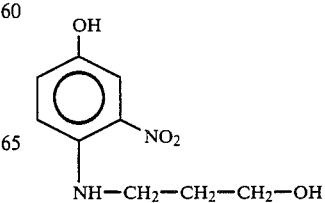

Stage (a) Preparation of γ-chloropropyl N-(2-nitro-4-hydroxyphenyl)-carbamate 77 g (0.5 mole) of 3-nitro-4-aminophenol are dissolved in 200 ml of dimethoxy ethane, 27 g of calcium carbonate are added, and 80 g (0.51 mole) of γ-chloropropyl chloroformate are added dropwise at 70° C. After 1 hour, the reaction mixture is filtered hot and the filtrate is stirred into 700 ml of ice-water, after which 128 g (93%) of the desired compound precipitate. The melting point is 103°–105° C., and after recrystallisation from toluene is 106° C.

Stage (b) Preparation of 4-(γ-hydroxypropyl)amino-3-nitrophenol: 110 g (0.4 mole) of the compound described in stage (a) are added in portions to a mixture of 180 g of 40% strength aqueous sodium hydroxide solution and 400 ml of ethanol at room temperature. The reaction mixture is then heated under reflux, adjusted to pH 6 with hydrochloric acid and concentrated completely. To remove the salts, the residue is taken up in ethanol and filtered, and is substantially concentrated again. The product which has precipitated is pressed off and dried and can be recrystallised from water, ethanol or ethyl acetate.

Yield: 71 g (84%), melting point: 110°–111° C.

Analysis for $C_9H_{12}N_2O_4$: calculated: C 50.94, H 5.70, N 13.20, found: 51.00, 5.50, 13.10.

UV/VIS: $\lambda_{max}=478$ nm ($\epsilon=5335$).

EXAMPLE 2

Preparation of 3-nitro-4-(n-propyl)aminophenol

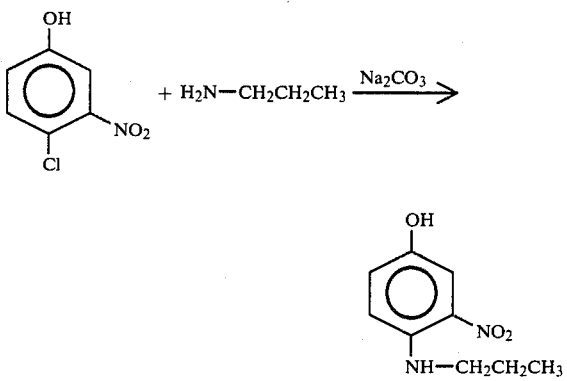

34.7 g (0.2 mole) of 4-chloro-3-nitrophenol, 21 g of sodium carbonate, 0.1 g of copper-I chloride and 20 g of n-propylamine are heated in a bath from room temperature up to a bath temperature of 120° C. After 5 hours, the reaction mixture is taken up in water, acidified (pH 2) with hydrochloric acid and extracted 3 times with ethyl acetate in order to remove unreacted starting material. After neutralisation, the aqueous phase is again extracted 3 times with ethyl acetate. After drying and concentration, these extracts give the desired product in the form of a red oil.

UV/VIS: $\lambda_{max}480$ nm ($\epsilon=5490$).

EXAMPLE 3

Preparation of 4-(β-hydroxypropyl)amino-3-nitrophenol

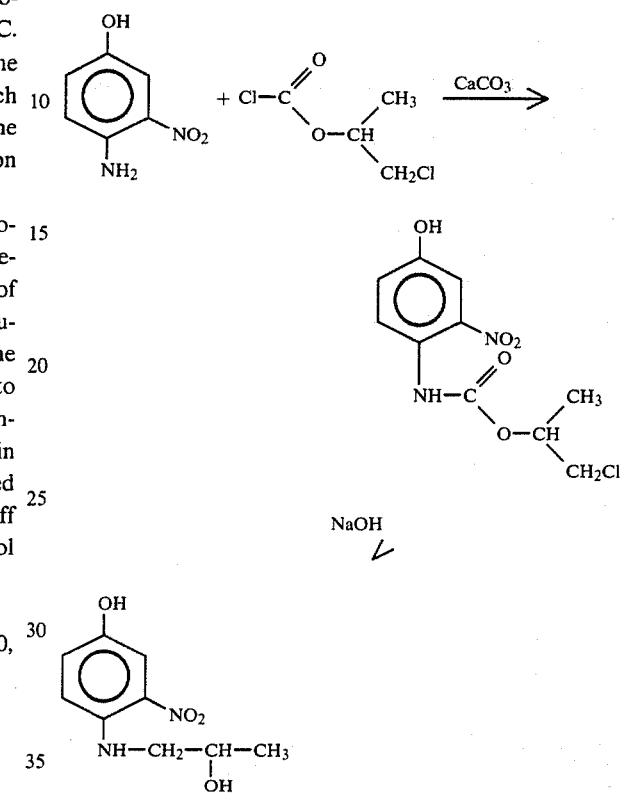

Stage (a) Preparation of β-chloropropyl N-(2-nitro-4-hydroxyphenyl)-carbamate 85 g (0.54 mole) of α-methyl-β-chloroethyl chloroformate are added dropwise to 77 g (0.5 mole) of 4-amino-3-nitrophenol and 27 g of calcium carbonate in 250 ml of dioxane at 70° C. After 2 hours at 90° C., the inorganic salts are filtered off hot and the filtrate is concentrated completely. The desired intermediate product is thereby obtained in the form of a reddish oil and is used as such in the following stage.

Stage (b) Preparation of 4-(β-hydroxypropyl)-amino-3-nitrophenol

The total amount of the oil obtained in the previous stage is taken up in 300 ml of ethanol and the mixture is added to 200 g of 40% strength aqueous sodium hydroxide solution. The mixture is then stirred under reflux for 1 hour, adjusted to pH 6.5 with hydrochloric acid and concentrated completely. After the residue has been boiled up with ethyl acetate, the salts have been filtered off and the filtrate has been concentrated down to the necessary volume for recrystallisation, 65 g of the desired product are obtained on cooling.

Yield over both stages: 61%.

Melting point: 146° C.

Analysis for $C_9H_{12}N_2O_4$: calculated: C 50.94, H 5.70, N 13.20, found: 50.90, 5.60, 13.20.

UV/VIS: $\lambda_{max}=474$ nm ($\epsilon=5218$).

EXAMPLE 4

Preparation of 4-amino-6-chloro-3-nitrophenol

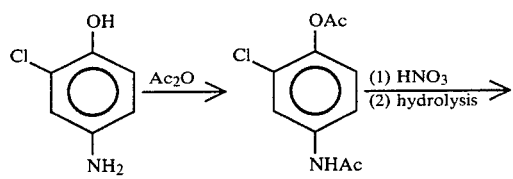

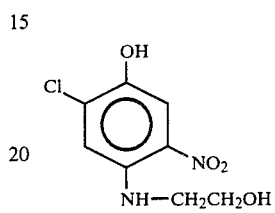

Ac = acetyl group

Stage (a) Preparation of O,N-bis-acetyl-(2-chloro-4-aminophenol)

143.5 g (1 mole) of 2-chloro-4-aminophenol are dissolved in 460 g of 20% strength aqueous sodium hydroxide solution and the solution is mixed with 900 g of ice. 225 g of acetic anhydride are poured in, whilst stirring thoroughly, stirring is continued for 2 hours and the product which has precipitated is collected on a suction filter, rinsed with 400 ml of water ethanol (5:1) and dried.

Yield: 210 g (92%), Melting point: 111°–112° C.

Stage (b) Preparation of O,N-bis-acetyl-(2-chloro-5-nitro-4-aminophenol).

227.5 g (1 mole) of the compound prepared in the previous stage are introduced in portions into 400 ml of fuming nitric acid at −10° C. The temperature is then allowed to rise to 0° C., the reaction solution is poured onto 2.5 liters of ice-water, and, after some time, the product which has precipitated is isolated.

Yield: 212 g (78%), Melting point: 128°–129° C.

Stage (c) Preparation of 6-chloro-3-nitro-4-aminophenols.

204 g (0.75 mole) of the compound prepared in stage (b) are heated at 100° C. in 2 liters of 2N sulphuric acid for 90 minutes. Whilst still warm, the mixture is adjusted to pH 5 with aqueous ammonia solution and the product which has precipitated is then isolated from the cooled solution.

Yield: 95 g (67%), Melting point: 184° C. (decomposition from 164° C.).

Analysis for $C_6H_5ClN_2O_3$: calculated: C 38.22, H 2.67, Cl 18.80, N 14.86, found: 38.70, 2.90, 18.60, 14.80.

UV/VIS: $\lambda_{max}$=442 nm ($\epsilon$=5027).

EXAMPLE 5

Preparation of 6-chloro-4-(β-hydroxyethyl-)amino-3-nitrophenol

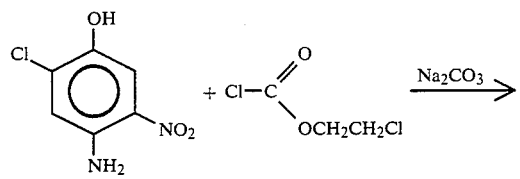

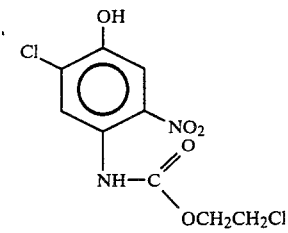

NaOH

Stage (a) Preparation of β-chloroethyl N-(5-chloro-4-hydroxy-2-nitrophenyl)-carbamate.

21 ml of β-chloroethyl chloroformate are added dropwise to 37.7 g (0.2 mole) of 6-chloro-3-nitro-4-aminophenol and 12 g of sodium carbonate in 130 ml of dioxane at 70° C. and the mixture is then heated at 90° C. for a further hour. After addition of 500 ml of water and stirring until cold, the mixture is extracted 3 times with methylene chloride and the extracts are dried and concentrated completely, after which 56 g (95%) of the product are obtained as a dark red oil, which crystallises completely, after some time, by trituration with toluene.

Melting point: 100°–102° C.

Stage (b) Preparation of 6-chloro-4-(β-hydroxyethyl)-amino-3-nitrophenol.

44.25 g (0.15 mole) of the compound obtained in the previous stage are reacted analogously to Example 1, stage (b); after recrystallisation from ethanol, 28.3 g (81%) of the desired product are obtained.

Melting point: 172°–173° C.

Analysis for $C_8H_9ClN_2O_4$: calculated: C 41.81, H 3.87, Cl 15.11, N 11.94, found: 41.80, 3.80, 14.90, 11.90.

UV/VIS: $\lambda_{max}$=462 nm ($\epsilon$=5927).

EXAMPLE 6

Preparation of 6-chloro-4-(γ-hydroxypropyl-)amino-3-nitrophenol

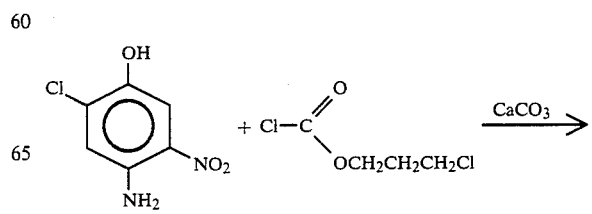

-continued

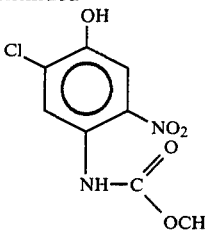

NaOH

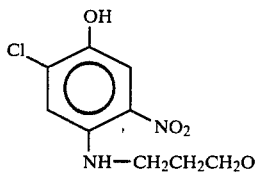

Stage (a) Preparation of γ-chloropropyl N-(5-chloro-4-hydroxy-2-nitrophenyl)-carbamate.

37.7 g (0.2 mole) of 6-chloro-3-nitro-4-aminophenol are dissolved in 120 ml of dimethoxyethane, 11 g of calcium carbonate are added and 32 g of γ-chloropropyl chloroformate are added dropwise at 70° C. After 1 hour at 90° C., the mixture is filtered hot and the filtrate is stirred into 300 ml of ice-water. The initially oily product crystallises after a short time.

Yield: 59 g (95%), Melting point: 107°–108° C.

Stage (b) Preparation of 6-chloro-4-(γ-hydroxypropyl)amino-3-nitrophenol.

46.35 g (0.15 mole) of the precursor are reacted analogously to Example 1, stage (b) and give 34 g (92%) of red crystals, which can be recrystallised from ethyl acetate.

Melting point: 128°–130° C.

Analysis for $C_9H_{11}ClN_2O_4$: calculated: N 11.36, found: 11.20.

UV: $\lambda_{max}=464$ ($\epsilon=6208$).

The compounds of the formula (I) according to the invention can be used both in basic and in neutral or acid hair-colouring agents and, because of their stability, can be used in oxidation colouring agents. They can furthermore also be used in hair-colouring agents which contain other direct-dyeing dyestuffs and in which dyestuff precursors may or may not also be present. A large number of direct-dyeing dyestuffs and dyestuff precursors which can be used for this purpose are known from earlier publications; for example Ullmann; Balsam and Sagarin; Cosmetics, Science and Technology, Volume 2, pages 308–310: J. Corbett; VII Congress JFSCC, Hamburg 1972, pages 559–599: J. Corbett; Hair Coloring; Rev. Prog. Coloration, 1973, Volume 4, pages 3–7: Schwarz, Kravitz, D'Angelo; Laboratory evaluation of some oxidation hair colour intermediates; Cosmetics and Toiletries 1979, Volume 94, page 47.

The pH of the hair-colouring agents according to the invention can vary, for example from about 2.5 to 12 and preferably from 3.5 to 10. If this colouring is carried out in an alkaline range, a compatible alkalising agent can be used in order to produce the desired pH. The amount of alkalising agent used can vary within a wide range and depends on the dyestuff, the alkalising agent specifically used and the desired pH. By way of illustration, the alkalising agent can vary from less than about 0.1 to about 15%, and preferably from about 0.25 to about 8%, based on the weight of the composition.

The alkalising agent is chosen such that it does not have an effect on the dyestuff used (that is to say it is compatible with the dyestuff) and does not precipitate the dyestuff. If human hair on the head is to be coloured, the alkalising agent must, under the conditions of use, neither be toxic nor damage the scalp in its highest concentration used in the composition. A prior test can be carried out with the alkalising agents in order to demonstrate their compatibility with the dyestuff or to reveal the possibility of toxicity or harmfulness.

Ammonium hydroxide is a suitable alkalising agent for the colouring of human hair, since it is economical and is non-toxic within a wide range. However, any other ammonia derivative can be used as the alkalising agent instead of or together with ammonia, such as an alkylamine, for example ethylamine or triethylamine, an alkanediamine, such as 1,3-diaminopropane, an alkanolamine, such as ethanolamine, a polyalkylenepolyamine, such as diethyltriamine, or a heterocyclic amine. An alkali metal hydroxide or alkaline earth metal hydroxide can also be used as the alkalising agent, at a concentration which produces no precipitate with one of the components of the composition. These compounds can also be used for colouring human hair as long as their concentration in the final dyestuff solution is below that which could possibly irritate the scalp.

Water-soluble organic amines of low volatility (boiling point above about 50° C.) and with less than 12 carbon atoms, such as isobutylamine, 2-ethylbutylamine, diethylamine and triethylamine, are preferred as the alkalising agents. The following alkalising agents are particularly suitable: (a) ammonia, (b) primary aliphatic diamines, such as ethylenediamine, 1,2-diaminopropane, 1,3-diaminopropane, diethylenetriamine, triethylenetetramine and 2,2'-iminodipropylamine, and (c) alkanolamines, such as ethanolamine, isopropanolamine, triethanolamine, triisopropanolamine, N-methyldiethanolamine, diisopropylethanolamine, dimethylisopropanolamine, 2-amino-2-methylpropane-1,3-diol and tri-(hydroxy-methyl)-methylamine.

The pH of the agent can be adjusted with an inorganic or organic acid or an acid salt which is compatible with the agent. Examples of acids or acid salts which may be mentioned are: sulphuric acid, formic acid, acetic acid, lactic acid, citric acid and tartaric acid, and ammonium sulphate, sodium dihydrogen phosphate and potassium bisulphate.

Water-soluble surface-active agents can also be used in the colouring agents used according to the invention. These can be anionic, non-ionic or cationic. The following may be mentioned to illustrate various types of water-soluble surface-active agents: higher alkylbenzenesulphonates, alkylnaphthalenesulphonates, sulphonated esters of alcohols and polybasic acids, taurates, fatty alcohol sulphates, sulphates of branched or secondary alcohols, alkyldimethylbenzylammonium chlorides and the like. Examples of particular wetting agents which may be mentioned are: lauryl sulphate, polyoxyethylene lauryl ester, myristyl sulphate, glyceryl monostearate, the sodium salt of palmitinmethyltaurin, cetylpyridinium chloride, lauryl sulphonate, myristyl sulphonate, the diethanolamine salt of lauric acid, polyoxyethylene stearate, stearyldimethylbenzylammonium chloride, sodium dodecylbenzenesulphonate, sodium nonylnaphthalenesulphonate, sodium dioctyl-sulphosuccinate, sodium N-methyl-N-oleyl-taurate, oleic acid esters of sodium isethionate, sodium dodecylsulphate, the sodium salt of 3,9-diethyl-tridecanol-6-sulphate and the like. The amount of water-soluble surface-active agent can vary within a wide range, such as about from 0.01 to 40%, based on the weight of the composition.

Besides other substances, such as, for example, emulsifiers, a thickening agent can also be incorporated into the present agent. One or more of these agents usually employed in hair-colouring agents may advantageously be used, such as sodium alginate or gum arabic, or cellulose derivatives, such as methylcellulose or the sodium salt of carboxymethylcellulose, or acrylic polymers, such as the sodium salt of polyacrylic acid, or inorganic thickening agents, such as bentonite. The amount of thickening agent can vary within a wide range, such as about from 0.1 to 20% by weight and preferably from about 0.5 to 5% by weight.

The proportions of dyestuffs of the formula (I) in the agents according to the invention can likewise vary within a wide range, such as from about 0.001% to more than about 10%. The agent preferably contains the colouring in a proportion which is effective in dyeing, which can vary from about 0.001 to 10%. The water content of the composition is generally the main component and can likewise be varied within a wide range, depending greatly on the amount of other additives. The water content can thus be only 10% and, preferably, about 50 to 90%.

The colouring agents according to the invention are aqueous agents. The expression "aqueous agent" is used here in its usual general sense, in that it comprises any agent according to the invention containing water. This includes true solutions of dyestuffs in an aqueous medium, either by themselves or in combination with other substances, which likewise have been dissolved or dispersed in the aqueous medium. The expression "aqueous agent" also includes any mixture of dyestuff with the aqueous medium either by itself or together with other constituents. The dyestuff can be colloidally dispersed in the medium or merely intimately mixed therein.

The expression "aqueous medium" used here includes any medium which contains water. The aqueous medium can therefore be an aqueous-alkaline, aqueous-neutral or aqueous-acid medium. Moreover, the aqueous medium can contain water and a solvent, such as aliphatic alcohols, aromatic alcohols, ethylene glycol dialkyl ethers and the like. The latter can be used as solubilising agents in order to promote solution of the dyestuff and/or another material.

The aqueous agents according to the invention can take many forms. Thus, they can be in the form of thin or thick, flowable liquids, pastes, emulsions, gels and the like.

Typical colouring agents which are particularly suitable for colouring human hair are given below:

1. ALKALINE AGENTS

| | General Range | Preferred Range |
|---|---|---|
| Dyestuffs | 0.001 to 10% | 0.001 to 3% |
| Surface-active agent | 0.01 to 40% | 0.10 to 20% |
| Alkali | 0.01 to 15% | 0.25 to 8% |
| Thickening agent | 0.1 to 20% | 0.5 to 5% |
| pH range | pH 7 to 12 | pH 7.5 to 10 |

| | General Range | Preferred Range |
|---|---|---|
| Water to 100% | | |

The dyestuffs must include at least one dyestuff of the formula (I) according to the invention. However, other directly absorbed dyestuffs can also additionally be present. Surface-active agents, alkalis, thickening agents and a combination thereof can be used in the proportions given in the table directly above. Directly absorbed dyestuffs which are suitable as additives are described in, for example: Ullman; Balsam and Sagarin; Cosmetics, Science and Technology, Volume 2, pages 308–10: J. Corbett; VII Congress JFSCC, Hamburg 1972, pages 559–599: J. Corbett; Hair Coloring; Rev. Prog. Coloration, 1973, Volume 4, pages 3–7: Schwarz, Kravitz, D'Angelo; Laboratory evaluation of some oxidation hair color intermediates; Cosmetics and Toiletries 1979, Volume 94, page 47.

2. ACID AGENTS

The acid agents are similar to the above alkaline agents, with the exception that the alkali is left out and acid is added up to a pH of 2.5 to 7, preferably of 3.5 to 6.5. The wetting agent can be anionic, cationic or non-ionic, or can consist of suitable mixtures thereof, and any of the abovementioned substances may be used. The choice of thickening agent is somewhat more restricted, that is to say to alkyl cellulose agents, such as methylcellulose, and inorganic agents. In certain cases, the wetting agents themselves can act as the thickening agent.

OXIDATION DYESTUFF COMPOSITIONS

The dyestuffs of the formula (I) used according to the invention are in general compatible with oxidation dyestuffs. Accordingly, they can be used in oxidation dyestuff agents which are particularly suitable for colouring human hair. Agents which can be used contain 1 to 5% of ammonia, 1 to 6% of hydrogen peroxide or urea peroxide, *0.005 to 2% of oxidation dyestuff components, 0.001 to 3% of the compound described in the above formula (I) and also wetting agents, thickeners and the like. The oxidation dyestuff components can be, for example, p-phenylenediamine, m-phenylenediamine, 2,5-diaminotoluene, resorcinol, hydroquinone, p-aminophenol, 2,4-diaminoanisole, p-aminodiphenylamine, 4,4'-diaminodiphenylamine and all the other developing and coupling components known for this purpose. The oxidation dyestuff composition can moreover also contain direct-dyeing dyestuffs, such as, for example, 4-nitro-2-aminophenol, 2-nitro-p-phenylenediamine, 4-nitro-o-phenylenediamine and all the other compounds known for this purpose. Suitable developing and coupling components and direct-dyeing dyestuffs are described, for example, in the abovementioned literature.
*in the ready-to-use formulation The hair-colouring agents according to the invention can be prepared by the conventional processes used in this field. Thus, they can be prepared by dissolving or suspending the dyestuff in water in the desired concentration. Water-miscible organic solvents may be used in order to facilitate solution of the dyestuffs; in this case, the dyestuff can first be dissolved in the solvent and the solution can then be diluted with water. Dispersion of the various constituents can likewise be facilitated by warming the composition to temperatures between 40° and 110° C., either before the dilution or thereafter.

The hair-colouring agents according to the invention can be used on the hair by the conventional techniques used in this field. In the case of use, for example, on hair growing on the human head, the agents can be applied with a brush, a sponge or other means of bringing about contact, such as immersion, until the hair is completely saturated with the composition.

The reaction time or the contact time between the colouring agent and the hair is not critical and can be within a relatively wide range used for colouring hair, such as periods of about 5 minutes to about 2 hours, preferably about 5 minutes to about 60 minutes. The temperature during colouring can likewise be within wide limits, as is customary in this field. Thus, the temperature during colouring can vary from about room temperature, for example about 20° C., to about 60° C. as the top limit, and preferably from about 20° C. to about 45° C.

The colouring compositions according to the invention are particularly suitable for colouring human hair on the head.

Every compound which falls under the formula (I) can be used in connection with the present invention. However, the following particular compounds may be mentioned for illustration: 4-($\gamma$-hydroxy-n-propyl-)amino-3-nitrophenol, 3-nitro-4-(n-propyl-)amino-phenol, 4-($\beta$-hydroxy-n-propyl-)amino-3-nitrophenol, 4-amino-6-chloro-3-nitrophenol, 6-chloro-4-($\beta$-hydroxyethyl)-amino-3-nitrophenol, 6-chloro-4-($\gamma$-hydroxy-n-propyl-)amino-3-nitrophenol.

The dyestuffs used in the compositions according to the invention can be prepared analogously to various known processes, as has already been demonstrated above.

The examples which follow illustrate the colouring of hair with the hair-colouring agents according to the invention. The methods used for colouring can be described as follows:

COLOURING METHOD A

Colouring of hair with agents in the alkaline range (pH 7 to about 12).

A mixture is prepared using certain amounts of the following components:

| Dyestuff | prescribed amount |
|---|---|
| Solvent | " |
| Emulsifier | " |
| Surface-active agent | " |
| Thickening agent | " |
| Alkaline agent | for establishing the prescribed pH value |

The dyestuff is wetted with the solvent and the abovementioned agents and 30 ml of water are added. The mixture is warmed to about 60° C., while stirring, until a uniform dispersion is formed. The mixture is then diluted to 100 ml with water and the pH is adjusted to the prescribed value of 7 or more.

The colouring agent thus obtained is applied to natural hair, hair which has turned grey, permanent-wave and bleached hair, and is left in contact with the hair for 20 minutes. The hair is then rinsed with clear water and styled in the usual way.

COLOURING METHOD B

Colouring of hair with agents in the acid range (pH 7 to about 3).

A mixture is prepared from the following components:

| Dyestuff | prescribed amount |
|---|---|
| Solvent | " |
| Emulsifier | " |
| Surface-active agent | " |
| Thickening agent | " |
| Acid agent | for establishing the prescribed pH value |

The dyestuff is wetted with the solvent and the other constituents are added individually; the mixture is made up to the volume with water and is warmed to about 50° C., while stirring, in order to form a uniform dispersion. The hair is coloured with this agent as described under Method A.

COLOURING METHOD C

Colouring of hair from a peroxide bath

The following agent is prepared:

| Dyestuff and dyestuff precursor | depending on the shade |
|---|---|
| Fatty alcohol | 26.5 g |
| Surface-active agent | 5.0 g |
| Fatty acid | 1.0 g |
| 25% strength ammonia | 10.0 g |
| Ethylenediaminetetraacetic acid | 0.3 g |
| Water to | 100 g |

A 40 g portion of this agent is mixed with 40 g of 6% strength hydrogen peroxide and the mixture is applied to natural hair, permanent-waved hair, hair which has turned grey and bleached hair, and is left on the hair at 30° C. for 30 minutes. The hair is then rinsed with clear water, shampooed and dried.

USE EXAMPLE 1

Hair is coloured with 0.2 g of dyestuff from Example 5 by Method A using 1 g of hydroxyethylcellulose, 5 g of monoethanolamine lauryl-sulphate, 1.5 g of stearyl alcohol and 5 g of propylene glycol. The pH of the agent was adjusted to 8.8.

Light-blonde hair is given a uniform light titian shade. If the equivalent amount of benzoyl alcohol is used instead of propylene glycol, a uniform titian shade which is more intense than when propylene glycol is used is obtained on light-blonde hair.

USE EXAMPLE 2

If 0.4 g of the same dyestuff is applied according to Method B, using 1 g of hydroxyethylcellulose, 5 g of sodium laurethsulphate, 1.8 g of cetyl alcohol and 4 g of methxybutanol and adjusting the agent to a pH of 6.5, light-blonde hair is coloured brick-red.

USE EXAMPLE 3

If 0.3 g of the dyestuff from Example 1 is used according to Method B in an agent as described in Use Example 1, grey or light-blonde hair is given a strong cherry-red colouration.

USE EXAMPLE 4

If 0.15 g of the dyestuff from Example 1, 0.1 g of p-phenylenediamine and 0.05 g of resorcinol are incorporated into an agent as described in Colouring Method C and the agent is used on natural grey hair, a reddish light-blonde shade is obtained.

USE EXAMPLE 5

If 0.15 g of the dyestuff from Example 6 is incorporated into an alkaline agent as described in Use Example 1 and this agent is used on medium-blonde hair, the hair is given a light rosewood shade.

USE EXAMPLE 6

Hair is coloured with 0.7 g of the dyestuff from Example 3 by Method A using 1.2 g of methylcellulose, 5 g of monoethanolamine lauryl-sulphate, 2 g of cetyl stearyl alcohol and 5 g of diethylglycol monoethyl ether. The pH of the agent is adjusted to 9.0. Light-brown hair is given a strong burgundy shade.

USE EXAMPLE 7

If 0.6 g of the dyestuff from Example 2 is incorporated into an agent as described in Use Example 6 and the agent is applied to light-brown hair, this is given a strong red shade.

USE EXAMPLE 8

Hair is dyed with 0.18 g of the dyestuff from Example 4 by Method B using 1.5 g of methyl cellulose, 4 g of sodium laurethsulphate, 2 g of cetyl alcohol and 6 g of propylene glycol. The pH of the agent is adjusted to 6.2. Medium-blonde hair is given a strong hazelnut shade.

USE EXAMPLE 9

If 0.9 g of the dyestuff from Example 3 and 0.4 g of 1,4,5,8-tetraaminoanthraquinone are incorporated into an agent as described in Use Example 6 and the agent is applied to light-to medium-brown hair, this is given a strong aubergine shade.

What is claimed is:

1. Compound of the formula

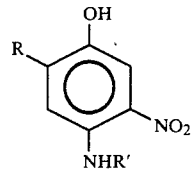

wherein R is Cl and R' is β-hydroxyethyl, α-methyl-β-hydroxyethyl, α-ethyl-β-hydroxyethyl, β-hydroxypropyl, γ-hydroxypropyl, β-hydroxy-n-butyl, or β-hydroxy-n-hexyl.

2. Compound according to claim 1 which is 6-chloro-4-(β-hydroxyethyl)amino-3-nitrophenol.

3. Compound according to claim 1 which is 6-chloro-4-(γ-hydroxy-n-propyl)amino-3-nitrophenol.

4. Aqueous coloring agent for hair or keratinic fibers, wherein said coloring agent contains at least one compound of formula (I) as a dyestuff

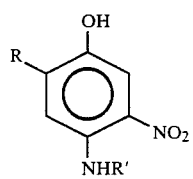

wherein R is Cl and R' is β-hydroxyethyl, α-methyl-β-hydroxyethyl, α-ethyl-β-hydroxyethyl, β-hydroxypropyl, γ-hydroxypropyl, β-hydroxy-n-butyl, or β-hydroxy-n-hexyl.

5. Agent according to claim 4 which is 6-chloro-4-(β-hydroxyethyl)amino-3-nitrophenol.

6. Agent according to claim 4 which is 6-chloro-4-(γ-hydroxy-n-propyl)amino-3-nitrophenol.

7. A method of dyeing hair or keratinic fibers comprising contacting the hair or keratinic fibers with an effective coloring amount of the aqueous coloring agent of claim 4 for a time and at a temperature sufficient to color the hair or fibers, and rinsing the coloring agent from the hair or fibers with water.

8. A method of dyeing hair or keratinic fibers comprising contacting the hair or keratinic fibers with an effective coloring amount of the aqueous coloring agent of claim 5 for a time and at a temperature sufficient to color the hair or fibers, and rinsing the coloring agent from the hair or fibers with water.

9. A method of dyeing hair or keratinic fibers comprising contacting the hair or keratinic fibers with an effective coloring amount of the aqueous coloring agent of claim 6 for a time and at a temperature sufficient to color the hair or fibers, and rinsing the coloring agent from the hair or fibers with water.

* * * * *